United States Defensive Publication [19] (H) [11] T998,005

Orwoll et al. [43] Sep. 2, 1980

[54] DESENSITIZED BENZOYL PEROXIDE COMPOSITIONS

[75] Inventors: Edward F. Orwoll, Langhorne, Pa.; Richard R. Boettcher, North Muskegon, Mich.

[73] Assignee: FMC Corporation, Philadelphia, Pa.

[21] Appl. No.: 20,677

[22] Filed: Mar. 15, 1979

[51] Int. Cl.[3] ..... C11D 3/395; C07C 179/10; C11D 7/54

[52] U.S. Cl. ..... 252/186; 8/111; 252/95; 568/559

[57] ABSTRACT

Provided are stabilized compositions of benzoyl peroxide and a method for their preparation.

The compositions comprise benzoyl peroxide and a desensitizer selected from the group consisting of a lower alkyl ester of 3,3-dimethyl-4-pentenoic acid and a lower alkyl ester of 4,6,6,6-tetrachloro-3,3-dimethylhexanoic acid, the desensitizer being present in an amount of at least 0.5 part by weight for each part by weight of benzoyl peroxide.

2 Claims, No Sheets Drawing,

10 Pages Specification

The file of this unexamined application may be inspected and copies thereof may be purchased (849 O.G. 1221, Apr. 9, 1968).